US006251367B1

(12) United States Patent
Platzek et al.

(10) Patent No.: US 6,251,367 B1
(45) Date of Patent: Jun. 26, 2001

(54) PARAMAGNETIC 3-,8-SUBSTITUTED DEUTEROPORPHYRIN DERIVATIVES, PHARMACEUTICAL AGENTS THAT CONTAIN THE LATTER, PROCESS FOR THEIR PRODUCTION, AND THEIR USE FOR MR IMAGING OF NECROSIS AND INFARCTION

(75) Inventors: Johannes Platzek; Ulrich Niedballa; Bernd Raduechel, all of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/359,043

(22) Filed: Jul. 23, 1999

Related U.S. Application Data (60) Provisional application No. 60/106,231, filed on Oct. 30, 1998.

(30) Foreign Application Priority Data

Jul. 24, 1998 (DE) .............................. 198 35 082

(51) Int. Cl.[7] .......................... A61K 49/10; A61K 49/12; C07D 487/22
(52) U.S. Cl. ........................ 424/9.362; 540/145
(58) Field of Search ........................ 540/145; 424/9.362

(56) References Cited

U.S. PATENT DOCUMENTS

| 5,053,503 | * 10/1991 | Dean et al. ........................ 540/474 |
| 5,275,801 | 1/1994 | Niedballa et al. .................. 424/1.65 |
| 5,284,647 | 2/1994 | Niedballa et al. ...................... 424/81 |
| 5,849,259 | 12/1998 | Hilger et al. ........................ 424/1.65 |
| 6,013,241 | 1/2000 | Marchal et al. .................... 424/1.65 |

FOREIGN PATENT DOCUMENTS

WO 9943317  2/1999 (WO).

OTHER PUBLICATIONS

Nakajima et al., Japan., Nucl. Med. Biol., 20 (2) 231–7., 1993.*

* cited by examiner

*Primary Examiner*—Richard L. Raymond
(74) *Attorney, Agent, or Firm*—Millen, White, Zelano & Branigan, P.C.

(57) ABSTRACT

Paramagnetic 3-,8-substituted deuteroporphyrin derivatives with various substituents in positions 13 and 17 of the porphyrin skeleton, are suitable as diagnostic agents for MR imaging of necrosis and infarction.

22 Claims, 4 Drawing Sheets

Figure 1A:
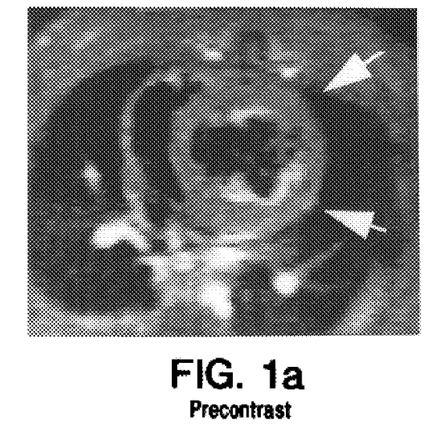

FIG. 1a
Precontrast

Figure 1B:
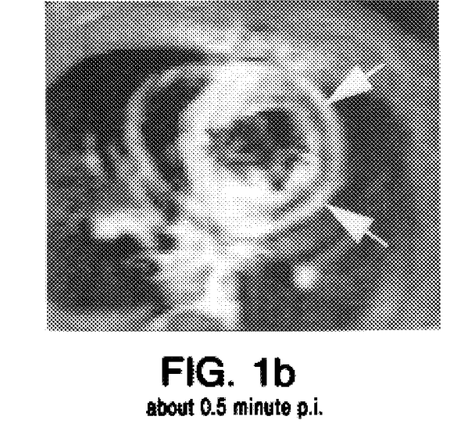

FIG. 1b
about 0.5 minute p.i.

Figure 1C:
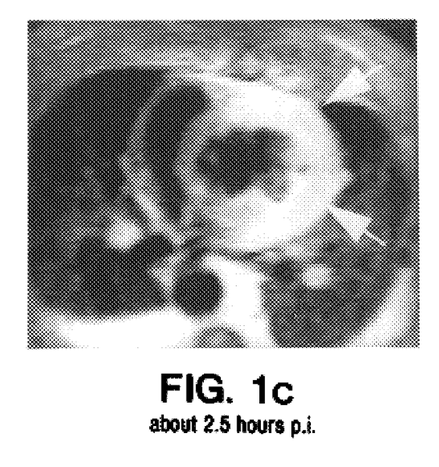

FIG. 1c
about 2.5 hours p.i.

Figure 1D:
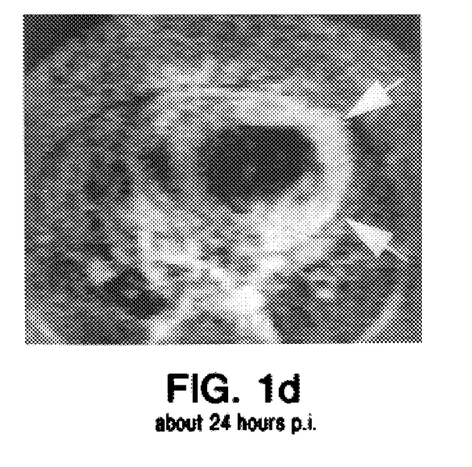

FIG. 1d
about 24 hours p.i.

Figure 1E:
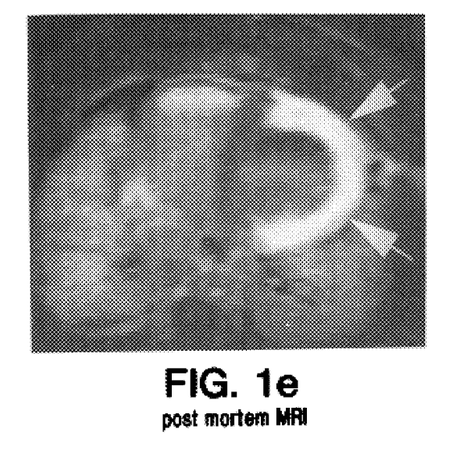

FIG. 1e
post mortem MRI

Figure 2A:
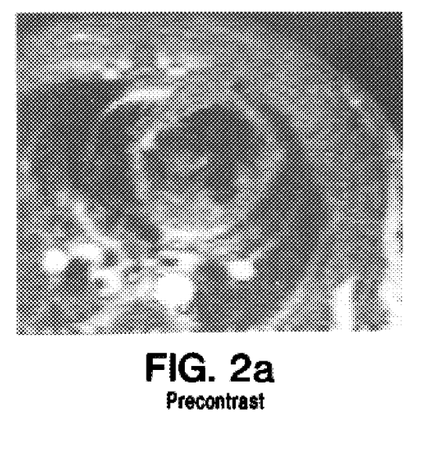

FIG. 2a
Precontrast

Figure 2B:
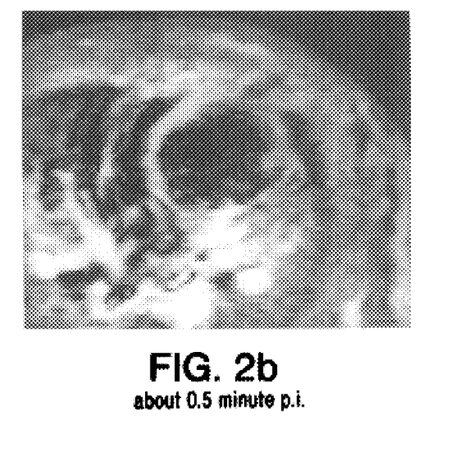

FIG. 2b
about 0.5 minute p.i.

Figure 2C:
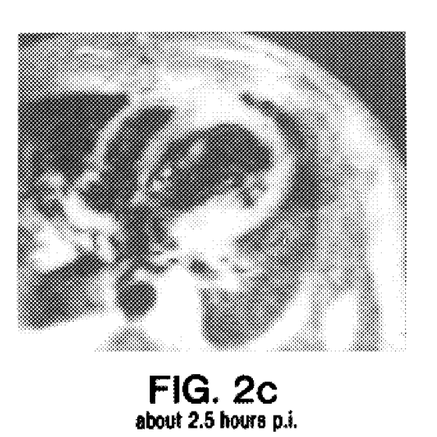

FIG. 2c
about 2.5 hours p.i.

Figure 2D:
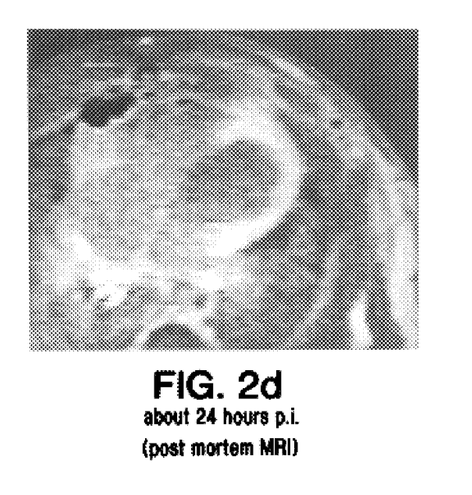

FIG. 2d
about 24 hours p.i.
(post mortem MRI)

Figure 3A:
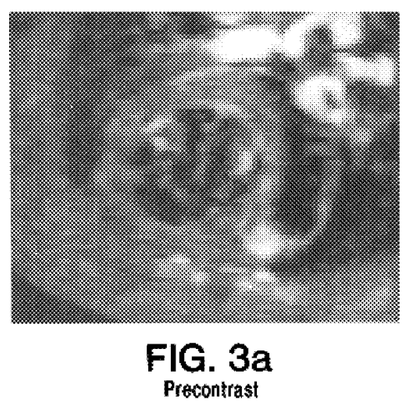

FIG. 3a
Precontrast

Figure 3B:
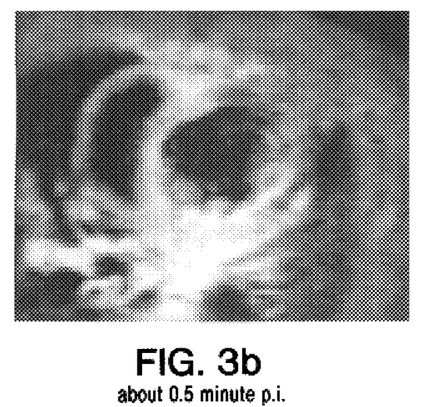

FIG. 3b
about 0.5 minute p.i.

Figure 3C:
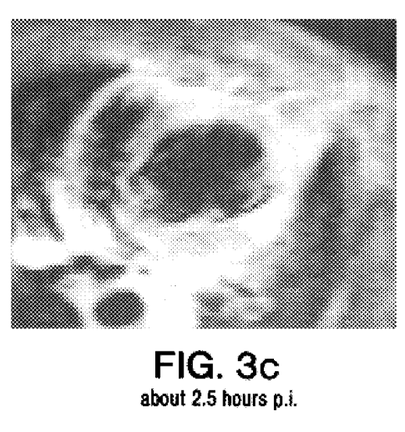

FIG. 3c
about 2.5 hours p.i.

Figure 3D:
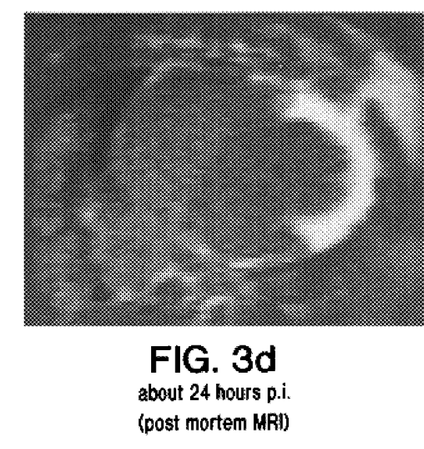

FIG. 3d
about 24 hours p.i.
(post mortem MRI)

FIG. 4

PARAMAGNETIC 3-,8-SUBSTITUTED DEUTEROPORPHYRIN DERIVATIVES, PHARMACEUTICAL AGENTS THAT CONTAIN THE LATTER, PROCESS FOR THEIR PRODUCTION, AND THEIR USE FOR MR IMAGING OF NECROSIS AND INFARCTION

The instant application claims benefit of U.S. Provisional Application No. 60/106,231, Oct. 30, 1998.

The invention relates to the subject that is characterized in the claims, i.e., paramagnetic 3-, 8-substituted deuteroporphyrin derivatives, pharmaceutical agents that contain the latter, process for their production, and their use for MR imaging of necrosis and infarction.

Detecting, locating, and monitoring necroses or infarctions is an important area in medicine. Thus, myocardial infarction is not a stationary process, but rather a dynamic process, which extends over a prolonged period—weeks to months. Infarction runs in phases, which are not strictly separate from one another but rather overlap. The first phase, the development of myocardial infarction, comprises the 24 hours after the infarction, during which the destruction spreads like a wave from the subendocardium to the myocardium. The second phase, the already existing infarction, comprises the stabilization of the area in which fiber formation (fibrosis) takes place as a healing process. The third phase, the healed infarction, begins after all destroyed tissue is replaced by fibrous scar tissue. During this period, extensive restructuring takes place.

Up until now, no specific and reliable process has been known that makes it possible to determine the current phase of a myocardial infarction in a live patient. To evaluate a myocardial infarction, it is of decisive importance to know how large the proportion of the tissue is that is extinct (lost) in the infarction and at what point the loss has taken place since the type of treatment depends on this knowledge. Infarctions take place not only in the myocardium but also in other tissues, especially in the brain.

While the infarction can be healed to a certain extent, in the case of a necrosis, locally limited tissue death, only the harmful sequelae for the residual organism can be prevented or at least mitigated. Necroses can occur in many ways: from injuries, chemicals, oxygen deficiency, or radiation.

As in the case of infarction, knowing the extent and type of necrosis is important for subsequent medical treatment. Attempts have thus already been made to improve the detection and locating of infarctions and necroses by using contrast media in the case of noninvasive processes such as scintigraphy or MRI. In literature, attempts to use porphyrins for necrosis imaging take up a good deal of space. The results that have been achieved, however, paint a contradictory picture. Winkelman and Hayes in Nature, 200, 903 (1967) describe the fact that Mn-5,10,15,20-tetrakis (4-sulfonatophenyl)-porphyrin (TPPS) accumulates selectively in the necrotic portion of a tumor. Lyon et al., Magn. Res. Med. 4, 24 (1987), however, observed that Mn-TPPS is distributed in the body, specifically in the kidney, liver, tumor and only in a small proportion in the muscles. In this case, it is advantageous for the concentration in the tumor to reach its maximum only on the fourth day, and this occurred only after the authors had increased the dose to 0.2 mmol/kg. The authors therefore also speak of a clearly nonspecific uptake of TPPS into the tumor.

Bockhorst et al. again report in Acta Neurochir. 1994 [Suppl.] 60, 347 that MnTPPS selectively binds to tumor cells. Foster et al., J. Nucl. Med. 26, 756 (1985) in turn found that In-111 5,10,15,20-tetrakis (4-N-methyl-pyridinium)-porphyrin (TMPyP) does not accumulate in the necrotic part, but rather in the living edge layers.

This does not necessarily indicate that a porphyrin-type-tissue-dependent interaction exists.

In Circulation, Vol. 90, No. 4, 1994, Part 2, Page 1468, Abstr. No. 2512, Ni et al. report that they can readily visualize infarction areas with an Mn-tetraphenyl-porphyrin (Mn-TTP) and a Gd-mesoporphyrin (Gd-MP).

Both substances are the subject of Application WO 95/31219.

In the case of scintigraphic processes, the dose that is used is in the nanomol range. The compatibility of the substances therefore plays only a subordinate role. With MR imaging, however, the dose is in the millimole range. Here, compatibility plays a quite decisive role.

The small acute compatibilities (LD50) that are determined for MnTPP or MnTPPS rule out their use in humans.

In addition, porphyrins—such as, e.g., Gd-mesoporphyrin—tend to be deposited in the skin, which results in photosensitization. This sensitization can last for days or even weeks. In the case of scintigraphic processes, this effect would be unimportant because of the low dose. Broad use of scintigraphic processes, however, is contraindicated owing to the fact that the resolution of a gamma camera is very much lower than that which can be achieved with MR imaging.

For MR imaging of myocardial infarction, the Gd-complexes of DTPA were also used (K. Bockhorst et al., Acta Neurochir. (1997) Suppl., 60:347–349); De Roos et al., Radiology 1989; 172:717–720) and its bis(methylamide) (M. Saeed et al., Radiology, 1992; 182:675–683). It turned out that both contrast media make it possible to differentiate between healthy and infarcted tissue only in a narrow time window. Comparable results were also obtained with the manganese compound of DTPA (Immunomedics, WO 94/22490) and DPDP (Radiology 1989; 172:59–64).

Weissleder et al., Radiology 1992; 182:675–683, who coupled antimyosin to iron oxides (MION), achieved a considerable improvement. Owing to its specific structure, this contrast medium is not suitable for necrosis imaging.

There is therefore an urgent need to have compounds for MR imaging of infarction and necrosis that:

are very well-tolerated, are not phototoxic, are chemically stable, are completely excreted, accumulate in necroses, are not concentrated in the skin, have a high relaxivity, exhibit high water solubility, provide a wide time window for measurement, make possible good differentiation between healthy and necrotic/infarcted tissue.

It has been found, surprisingly enough, that porphyrin complexes that consist of a ligand of general formula I (I)

and at least one ion of an element of atomic numbers 20–32, 37–39, 42–51 or 57–83, in which M stands for a paramagnetic ion, $R^1$ stands for a hydrogen atom, for a straight-chain $C_1$–$C_6$ alkyl radical, a $C_7$–$C_{12}$ aralkyl radical, or for a group OR' in which R' is a hydrogen atom or a $C_1$–$C_3$ alkyl radical, $R^2$ stands for $R^3$, a group —CO—Z or a group —(NH)$_o$—(A)$_q$—NH—D, in which Z is a group —OL, with L in the meaning of an inorganic or organic cation or a $C_1$–$C_4$ alkyl radical, A means a phenylenoxy group or a $C_1$–$C_{12}$ alkylene group that is optionally interrupted by one or more oxygen atoms or a $C_7$–$C_{12}$ aralkylene group, o and q, independently of one another, mean numbers 0 or 1, and D means a hydrogen atom or a group —CO—A—(COOL)$_o$—(H)$_m$, with m equal to 0 or 1 and provided that the sum of m and o is equal to 1,

$R^3$ stands for a group —(C=Q)(NR$^4$)$_o$—(A)$_q$—(NR$^5$)—K, in which Q stands for an oxygen atom or for two hydrogen atoms, $R^4$ means a group —(A)$_q$—H, and

K means a complexing agent of general formula (IIa), (IIb), (IIc), (IId) (IIe), or (IIf), whereby if K is a complexing agent of formula (IIa), $R^5$ has the same meaning as $R^4$, and if K is a complexing agent of formula (IIb), (IIc), (IId), (IIe), or (IIf), $R^5$ has the same meaning as D, provided that a direct oxygen-nitrogen bond is not allowed, and K stands for a complexing agent of general formula (IIa), (IIb), (IIc), (IId), (IIe) or (IIf)

(IIa)

(IIb)

(IIc)

(IId)

(IIe)

(IIf)

in which q has the above-indicated meaning,

A' has the meaning that is indicated for A, $R^6$ stands for a hydrogen atom, a straight-chain or branched $C_1$–$C_7$ alkyl group, a phenyl or benzyl group, $A^2$ stands for a phenylene, —$CH_2$—NHCO—$CH_2$—CH($CH_2COOH$)—$C_6H_4$-β-, —$C_6H_4$—O—$(CH_2)_{0-5}$-β-, —$C_6H_4$—$(OCH_2CH_2)_{0-1}$—N($CH_2COOH$)—$CH_2$-β- group or a $C_1$–$C_{12}$ alkylene or $C_7$–$C_{12}$ alkylene group that is optionally interrupted by one or more oxygen atoms, 1 to 3 —NHCO or 1 to 3 —CONH groups and/or substituted with 1 to 3 —$(CH_2)_{0-5}COOH$ groups, whereby β stands for the binding site to X, X stands for a —CO— or NHCS group and L$^1$, L$^2$, L$^3$ and L$^4$, independently of one another, stand for a hydrogen atom or a metal ion equivalent of an element of the above-mentioned atomic numbers, provided that at least two of these substituents stand for metal ion equivalents, and that other anions are present to compensate for optionally present charges in the metalloporphyrin and in which free carboxylic acid groups that are not required for complexing can also be present as salts with physiologically compatible inorganic and/or organic cations or as esters or as amides, are suitable, surprisingly enough, for MR imaging of necrosis and infarction. They meet the requirements (see above) that are to be imposed on such compounds. They can also be used for therapy monitoring in photodynamic therapy (PDT).

As a paramagnetic ion in the porphyrin skeleton, the porphyrin complexes according to the invention contain the iron (III), manganese(III), copper(II), cobalt(III), chromium (III), nickel(II) or vanadyl(II) ion, whereby the first three mentioned above are preferred.

Surprisingly enough, the complexes according to the invention show a considerably higher relaxivity compared to the previously known, structurally similar compounds. Since the relaxivity can be considered as a yardstick for the contrast medium action of a compound, a comparable, positive signal effect even at a low dose can be carried out with use of the complexes according to the invention in the area of NMR diagnosis. This significantly increases the safety margin, for which the product of relaxivity and compatibility can be considered as a guide value.

If an ion that is bonded in the porphyrin is present in a higher oxidation stage than +2, the excess charge(s) are compensated for by, e.g., anions of organic or inorganic acids, preferably by acetate, chloride, sulfate, nitrate, tartrate, succinate and maleate ions or by negative charges that are present in R$^2$ and/or R$^3$.

The carboxyl groups, which are not required for the complexing of metal ions, optionally can be present as esters, as amides or as salts of inorganic or organic bases. Suitable ester radicals are those with 1 to 6° C. atoms, preferably the ethyl esters; suitable inorganic cations are, for example, the lithium ion and the potassium ion and especially the sodium ion. Suitable cations of organic bases are those of primary, secondary or tertiary amines, such as, for example, ethanolamine, diethanolamine, morpholine, glucamine, N,N-dimethylglucamine, especially meglumine.

q preferably stands for the number 0;
A preferably stands for
—CH$_2$—CH$_2$—
—CH$_2$CH$_2$CH$_2$—
—CH$_2$CH$_2$CH$_2$CH$_2$—

—CH$_2$CH$_2$—O—CH$_2$CH$_2$—
—CH$_2$CH$_2$—O—CH$_2$CH$_2$—O—CH$_2$CH$_2$—

—(CH$_2$)$_5$—
—(CH$_2$)$_6$—
—(CH$_2$)$_{10}$—
—(CH$_2$CH$_2$—O)$_2$—CH$_2$CH$_2$—O—CH$_2$CH$_2$—
—CH$_2$—O—C$_6$H$_4$—

R$^2$ and R$^3$ respectively preferably stand for the groups —CONHNHK, —CONH(CH$_2$)$_2$NHK, —CONH(CH$_2$)$_3$NHK, —CONH(CH$_2$)$_4$NHK and —CONH (CH$_2$)$_2$O(CH$_2$)$_2$NHK, whereby the first group is preferred, and R$^2$ and R$^3$ preferably stand for the same radical.

A$^2$ preferably stands for an alkylene, —CH$_2$—, —(CH$_2$)$_2$—, —CH$_2$OC$_6$H$_4$-β-, —CH$_2$OCH$_2$—, —C$_6$H$_4$—, —CH$_2$—NHCO—CH$_2$—CH (CH$_2$COOH)—C$_6$H$_4$-β, —C$_6$H$_4$—OCH$_2$-β or —C$_6$H$_4$—OCH$_2$CH$_2$—N(CH$_2$COOH)CH$_2$-β group, whereby β stands for the binding site to X.

X preferably stands for the CO group.

R$^6$ preferably stands for a hydrogen atom or a methyl group.

As special compounds, {mu-[(16,16'-[chloromanganese (III)-7,12-diethyl-3,8,13,17-tetramethylporphyrin-2,18-diyl]-bis[3,6,9-tris(carboxymethyl)-11,14-dioxo-3,6,9,12, 13-pentaazahexadecanoato]}(8-)]}-digadolinato(2-), -disodium, {mu[{16,16'-[chloroiron(III)-7,12-diethyl-3,8, 13,17-tetramethylporphyrin-2,18-diyl]-bis[3,6,9-tris (carboxymethyl)-11,14-dioxo-3,6,9,12,13-pentaazahexadecanoato]}(8-)]}-digadolinato(2-), -disodium, {mu[{16,16'-[copper(II)-7,12-diethyl-3,8,13,17-tetramethylporphyrin-2,18-diyl]-bis[3,6,9-tris (carboxymethyl)-11,14-dioxo-3,6,9,12,13-pentaazahexadecanoato]}(8-)]}-digadolinato(2-), -disodium can be mentioned.

As complexing agent radical K, preferably derivatives of diethylenetriaminepentaacetic acid and of 1,4,7,10-tetraazacyclododecane-1,4,7-triacetic acid, which are bonded via a linker to the respective porphyrin, can be mentioned.

The production of the complex compounds of general formula I is carried out according to methods that are known in the literature (see, e.g., DE 4232925 for IIa and IIb; see, e.g., DE 19507822, DE 19580858 and DE 19507819 for IIIc; see, e.g., U.S. Pat. No. 5,053,503, WO 96/02669, WO 96/01655, EP 0430863, EP 255471, U.S. Pat. No. 5,277,895, EP 0232751, U.S. Pat. No. 4,885,363 for IId, IIe and IIf).

The compounds in which R$^2$ and R$^3$ stand for CONHNHK groups are preferred. The synthesis of the 3,3'-(7,12-diethyl-3,8,13,17-tetramethylporphin-2,18-diyl) di(propanohydrazide) that is required as an educt for this purpose is described in Z. Physiol Chem. 241, 209 (1936).

The introduction of the desired metals (e.g., Mn) in the porphyrins is carried out according to methods that are known in the literature (e.g., The Porphyrins, ed. D. Dolphin, Academic Press, New York 1980, Vol. V, p. 459; DE 4232925), whereby basically the following can be mentioned:

a) the substitution of pyrrolic NH's (by heating metal-free ligands with the corresponding metal salt, preferably acetate, optionally with the addition of acid-buffering means, such as, e.g., sodium acetate, in a polar solvent) or b) the "recomplexing," in which a metal that is already complexed by a ligand is displaced by the desired metal.

As solvents, primarily polar solvents, such as, e.g., methanol, glacial acetic acid, dimethylformamide, chloroform and water are suitable.

The introduction of paramagnetic metal M in the porphyrin system can be carried out before or after complexing agent radical K is linked. As a result, an especially flexible procedure for the synthesis of the compounds according to the invention is made possible.

The chelation of radical K is carried out in a way that is known in the literature (see, e.g., DE 34 01 052) by the metal oxide or metal salt (e.g., the nitrate, acetate, carbonate, chloride or sulfate) of the respectively desired metal being suspended or dissolved in polar solvents such as water or aqueous alcohols and being reacted with the corresponding amount of the complexing ligand. If desired, acid hydrogen atoms or acid groups that are present can be substituted by cations of inorganic and/or organic bases or amino acids.

Neutralization is carried out in this case with the aid of organic bases, such as, e.g., alkali or alkaline-earth hydroxides, -carbonates or -bicarbonates and/or organic bases such as, i.a., primary, secondary and tertiary amines, such as, e.g., ethanolamine, morpholine, glucamine, N-methyl- and N,N-dimethylglucamine, as well as basic amino acids, such as, e.g., lysine, arginine and ornithine or of amides of originally neutral or acidic amino acids.

For the production of neutral complex compounds, for example, enough of the added bases can be added to the acid complex salts in aqueous solution or suspension to ensure that the neutral point is reached. The solution that is obtained can then be evaporated to the dry state in a vacuum. It is often advantageous to precipitate the neutral salts that are formed by adding water-miscible solvents, such as, for example, lower alcohols (e.g., methanol, ethanol, isopropanol), lower ketones (e.g., acetone), polar ethers (e.g., tetrahydrofuran, dioxane, 1,2-dimethoxyethane) and to obtain easily isolated and readily purified crystallizates. It has proven especially advantageous to add the desired base as early as during the complexing of the reaction mixture and thus to eliminate a process step.

If the acidic complex compounds contain several free acid groups, it is often suitable to produce neutral mixed salts that contain both inorganic and organic cations as counterions.

This can be done by, for example, the complexing ligands being reacted in aqueous suspension or solution with the oxide or salt of the element that yields the central ion and half of the amount of an organic base that is required for neutralization, the complex salt that is formed being isolated, optionally purified and then mixed with the required amount of inorganic base for complete neutralization. The sequence in which the base is added can also be reversed.

Another way of obtaining neutral complex compounds consists in converting the remaining acid groups in the complex completely or partially into esters. This can be done by subsequent reaction on the finished complex (e.g., by exhaustive reaction of the free carboxy groups with dimethylsulfate).

The production of the pharmaceutical agents according to the invention is also carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, e.g., tromethamine), small additions of complexing agents (such as, e.g., diethylenetriaminepentaacetic acid) or, if necessary, electrolytes such as, e.g., sodium chloride, or, if necessary, antioxidants, such as, e.g., ascorbic acid.

If suspensions or solutions of the agents according to the invention in water or in physiological salt solution are desired for enteral administration or other purposes, they are mixed with one or more adjuvant(s) that are commonly used in galenicals (e.g., methylcellulose, lactose, mannitol) and/or surfactant(s) (e.g., lecithins, Tween(R), Myrj (R)) and/or flavoring substances for taste correction (e.g., ethereal oils).

Basically, it is also possible to produce the pharmaceutical agents according to the invention even without isolating the complex salts. In any case, special care must be taken to perform the chelation in such a way that the salts according to the invention and salt solutions are virtually free of noncomplexed metal ions that have a toxic effect.

This can be ensured, for example, with the aid of color indicators, such as xylenol orange, by control titrations during the production process. The invention therefore also relates to a process for the production of complex compounds and their salts. As a final precaution, there remains purification of the isolated complex salt.

The pharmaceutical agents according to the invention contain preferably 20 $\mu$mol/L to 200 mmol/L of the complex salt and are generally dosed in amounts of 1 $\mu$mol to 2 mmol/kg of body weight, both in their use for MR imaging of necrosis and infarction and for therapy monitoring using MRI diagnosis. They are intended for enteral and parenteral administration or are administered with the methods of interventional radiology.

The agents according to the invention meet the varied requirements for suitability as agents for MRI contrast media. After administration, they are thus extremely well suited for enhancing the informational value of the image that is obtained with the aid of a nuclear spin tomograph by increasing the signal intensity. They also show the high effectiveness that is necessary to load the body with the smallest possible amounts of foreign substances and the good compatibility that is necessary to maintain the noninvasive nature of the studies.

The compounds of general formula I are also suitable for visualizing the intravascular space (blood-pool).

The good water-solubility of the agents according to the invention allows the production of highly concentrated solutions to ensure that the volume burden of the circulation is kept within justifiable limits and to offset the dilution by bodily fluids.

In addition, the agents according to the invention have not only high stability in vitro but also a surprisingly high stability in vivo, so that a release or an exchange of the ions, which are inherently toxic and not covalently bonded in the complexes, can be disregarded within the time that it takes for the contrast media to be completely excreted.

The invention is explained by the examples below.

EXAMPLE 1 a) Acetato [7,12-diethyl-3,8,13,17-tetramethylporphyrin-2,18-dipropionylhydrazinato(2-)-K N21, K N22, K N23, K N24]-iron 1190 mg (2 mmol) of 3,3'-(7,12-diethyl-3,8,13,17-tetramethylporphyrin-2,18-diyl)-di(propanohydrazide), produced analogously to H. Fischer, E. Haarer and F. Stadler, Z.

Physiol. Chem. 241, 209 (1936), and 706.36 mg (2 mmol) of iron(III)-acetylacetonate are heated in 150 ml of acetic acid/100 ml of chloroform for 5 hours to 70° C. Then, it is concentrated by evaporation in a vacuum, the residue is suspended in water, filtered off and washed with water. The dried crude product is recrystallized from pyridine/diethyl ether.

Yield: 1.25 g (89% of theory) of a reddish-brown powder

Elementary analysis:

| | | | | |
|---|---|---|---|---|
| Cld: | C 61.10 | H 6.12 | N 15.84 | Fe 7.89 |
| Fnd: | C 60.95 | H 6.31 | N 15.70 | Fe 7.68 | b) Acetato [7,12-diethyl-3,8,13,17-tetramethyl-2,18-bis{3,6,16-trioxo-8,11,14-tris(carboxymethyl) 17-oxa-4,5,8,11,14-pentaazanonadec-1-yl}porphyinato(3-)]-iron 806.8 mg (2 mmol) of 3-ethoxy-carbonylmethyl-6-[2—(2,6-dioxomorpholino)ethyl]-3,6-diazaoctanedioic acid (DTPA-monoethylester-monanhydride) is suspended in 250 ml of absolute dimethylformamide. It is covered with a layer of nitrogen, 1.0 g (10 mmol) of triethylamine and 707 mg (1 mmol) of the title compound of Example 1$a$ are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0–30%).

Yield: 1.62 g (93% of theory) of a reddish-brown powder

Water content: 5.2%

Elementary analysis (relative to anhydrous substance):

| | | | | |
|---|---|---|---|---|
| Cld: | C 53.93 | H 6.19 | N 12.95 | Fe 3.69 |
| Fnd: | C 53.75 | H 6.37 | N 12.81 | Fe 3.49 | c) Chloro [7,12-diethyl-3,8,13,17-tetramethyl-2,18-bis{3,6,18-trioxo-8,11,14-tris(carboxymethyl)-4,5,8,11,14-pentaazahexadecanato}porphinato(3-)]-iron 1.59 g (0.660 mmol) of the ligand that is produced under Example 1b is dissolved in 400 ml of water. By adding 10 mol of aqueous sodium hydroxide solution, it is set at pH 13 and stirred for 5 hours at room temperature. After the ester groups have been completely saponified, a pH of 3 is set with concentrated hydrochloric acid. It is evaporated to the dry state in a vacuum. The residue is chromatographed on silica gel RP 18 (eluant: $H_2O$/tetrahydrofuran/gradient).

Yield: 0.89 g (95% of theory) of a reddish-brown powder

Water content: 6.1%

Elementary analysis (relative to anhydrous substance):

| | | | | | |
|---|---|---|---|---|---|
| Cld: | C 51.90 | H 5.76 | N 13.67 | Fe 3.89 | Cl 2.47 |
| Fnd: | C 51.75 | H 5.88 | N 13.54 | Fe 3.75 | Cl 2.38 | d) {Mu-[{16,16'-[chloroiron(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium 0.86 g (0.599 mmol) of the ligand that is produced under Example 1c is dissolved in 400 ml of water, and 316.3 mg (1.2 mmol) of gadolinium chloride and 2N aqueous sodium hydroxide solution are alternately added in portions in such a way that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18 (eluant: $H_2O$/tetrahydrofuran: 0–30%).

Yield: 1.04 g (98% of theory) of a reddish-brown powder

Water content: 6.9%

Elementary analysis (relative to anhydrous substance):

| | | | | | | | |
|---|---|---|---|---|---|---|---|
| Cld: | C 41.67 | H 4.17 | N 10.97 | Gd 17.60 | Fe 3.13 | Cl 1.98 | Na 2.61 |
| Fnd: | C 41.48 | H 4.32 | N 10.80 | Gd 17.43 | Fe 3.07 | Cl 1.78 | Na 2.38 |

EXAMPLE 2 a) Acetato [7,12-diethyl-3,8,13,17-tetramethylporphyrin-2,18-dipropionyl-hydrazinato(2-)-K N21, K N22, K N23, K N24]-manganese 1190 mg (2 mmol) of 3,3'-(7,12-diethyl-3,8,13,17-tetramethylporphyrin-2,18-diyl)-di(propanohydrazide), produced analogously to H. Fischer, E. Haarer and F. Stadler, Z. Physiol. Chem. 241, 209; (1936), and 704.5 mg (2 mmol) of manganese(III)-aetylacetonate-dihydrate are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.29 g (91% of theory) of a reddish-brown powder

Elementary analysis:

| | | | | |
|---|---|---|---|---|
| Cld: | C 61.18 | H 6.13 | N 15.86 | Mn 7.77 |
| Fnd: | C 61.03 | H 6.29 | N 15.75 | Mn 7.58 | b) Acetato [7,12-diethyl-3,8,13,17-tetramethyl-2,18-bis{3,6,18-trioxo-8,11,14-tris(carboxymethyl)-17-oxa-4,5,8,11,14-pentaazanonadec-1-yl}porphyrinato(3-)]-manganese 806.8 mg (2 mmol) of 3-ethoxy-carbonylmethyl-6-[2-(2, 6-dioxomorpholino)ethyl]-3,6-diazaoctanedioic acid (DTPA-monoethylester-monoanhydride) is suspended in 250 ml of absolute dimethylformamide. It is covered with a layer of nitrogen, 1.0 g (10 mmol) of triethylamine and 706 mg (1 mmol) of the title compound of Example 2a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0–30%).

Yield: 1.35 g (89% of theory) of a reddish-brown powder

Water content: 5.9%

| Elementary analysis (relative to anhydrous substance): | | | | |
|---|---|---|---|---|
| Cld: | C 53.96 | H 6.19 | N 12.96 | Mn 3.63 |
| Fnd: | C 53.83 | H 6.34 | N 12.81 | Mn 3.49 | c) Chloro [7,12-diethyl-3,8,13,17-tetramethyl-2,18-bis{3,6, 18-trioxo-8,11,14-tris(carboxymethyl)-4,5,8,11,14-pentaazahexadecanoato}porphinato(3-)]-manganese 1.31 g (0.865 mmol) of the ligand that is produced under Example 2b is dissolved in 400 ml of water. By adding 10 mol of aqueous sodium hydroxide solution, it is set at pH 13 and stirred for 5 hours at room temperature. After the ester groups have been completely saponified, a pH of 3 is set with concentrated hydrochloric acid.

It is evaporated to the dry state in a vacuum. The residue is chromatographed on silica gel RP 18 (eluant: $H_2O$/tetrahydrofuran/gra Yield: 1.15 g (93% of theory) of a reddish-brown powder Water content: 7.2%

| Elementary analysis (relative to anhydrous substance): | | | | | |
|---|---|---|---|---|---|
| Cld: | C 51.93 | H 5.76 | N 13.68 | Mn 3.83 | Cl 2.47 |
| Fnd: | C 51.81 | H 5.93 | N 13.49 | Mn 3.70 | Cl 2.32 | d) {Mu-[{16,16'-[chloromanganese(III)-7,12-diethyl-3,8, 13,17-tetramethyl-porphyrin-2,18-diyl]-bis[3,6,9-tris(carboxymethyl)-11,14-dioxo-3,6,9,12,13-pentaazahexadecanoato]}(8-)]}-digadolinato(2-), -disodium 1.12 g (0.781 mmol) of the ligand that is produced under Example 2c is dissolved in 400 ml of water, and 411.8 mg (1.56 mmol) of gadolinium chloride and 2N aqueous sodium hydroxide solution are alternately added in portions in such a way that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18 (eluant: $H_2O$/tetrahydrofuran: 0–30%).

Yield: 1.35 g (97% of theory) of a reddish-brown powder

Water content: 6.5%

| Elementary analysis (relative to anhydrous substance): | | | | | | | |
|---|---|---|---|---|---|---|---|
| Cld: | C 41.69 | H 4.18 | N 10.98 | Gd 17.61 | Mn 3.08 | Cl 1.98 | Na 2.57 |
| Fnd: | C 41.48 | H 4.33 | N 10.81 | Gd 17.50 | Mn 2.89 | Cl 1.85 | Na 2.34 |

EXAMPLE 3 a) Acetato[7,12-diethyl-3,8,13,17-tetramethylporphyrin-2, 18-dipropionylhydrazinato(2-)-K N21, K N22, K N23, K N24]-cobalt 1190 mg (2 mmol) of 3,3'-(7,12-diethyl-3,8,13,17-tetramethylporphyrin-2,18-diyl)-di(propanohydrazide), produced analogously to H. Fischer, E. Haarer and F. Stadler, Z. Physiol. Chem. 241, 209 (1936), and 712.52 mg (2 mmol) of cobalt(III) acetylacetonate are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.31 g (92% of theory) of a reddish-brown powder

| Elementary analysis: | | | | |
|---|---|---|---|---|
| Cld: | C 60.84 | H 6.10 | N 15.77 | Co 8.29 |
| Fnd: | C 60.71 | H 6.29 | N 15.58 | Co 8.14 | b) Acetato[7,12-diethyl-3,8,13,17-tetramethyl-2,18-bis{3,6, 18-trioxo-8,11,14-tris(carboxymethyl)-17-oxa-4,5,8,11, 14-pentaazanonadec-1-yl}porphinato(3-)]-cobalt 806.8 mg (2 mmol) of 3-ethoxy-carbonylmethyl-6-[2—(2,6-dioxomorpholino)ethyl]-3,6-diaza octanedioic acid (DTPA-monoethylester-monoanhydride) is suspended in 250 ml of absolute dimethylformamide. It is covered with a layer of nitrogen, 1.0 g (10 mmol) of triethylamine and 710 mg (1 mmol) of the title compound of Example 3a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0.30%)

Yield: 1.32 g (87% of theory) of a reddish-brown powder

Water content: 6.7%

| Elementary analysis (relative to anhydrous substance): | | | | |
|---|---|---|---|---|
| Cld: | C 53.82 | H 6.18 | N 12.92 | Co 3.88 |
| Fnd: | C 53.72 | H 6.35 | N 12.81 | Co 3.69 | c) Chloro [7,12-diethyl-3,8,13,17-tetramethyl-2,18-bis{3,6, 18-trioxo-8,11,14-tris(carboxymethyl)-4,5,8,11,14-pentaazahexadecanoato}porphinato(3-)]-cobalt 1.28 g (0.844 mmol) of the ligand that is produced under Example 3b is dissolved in 400 ml of water. By adding 10 mol of aqueous sodium hydroxide solution, it is set at pH 13 and stirred for 5 hours at room temperature. After the ester groups have been completely saponified, a pH of 3 is set with concentrated hydrochloric acid. It is evaporated to the dry state in a vacuum. The residue is chromatographed on silica gel RP 18 (eluant: $H_2O$/tetrahydrofuran/gradient).

Yield: 1.15 g (95% of theory) of a reddish-brown powder
Water content: 4.9%

| Elementary analysis (relative to anhydrous substance): | | | | | |
|---|---|---|---|---|---|
| Cld: | C 51.79 | H 5.75 | N 13.64 | Co 4.10 | Cl 2.47 |
| Fnd: | C 51.60 | H 5.89 | N 13.51 | Co 3.97 | Cl 2.35 | d) {Mu-[{16,16'-[chlorocobalt(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium 1.12 g (0.779 mmol) of the ligand that is produced under Example 3c is dissolved in 400 ml of water, and 410.6 mg (1.59 mmol) of gadolinium chloride and 2N aqueous sodium hydroxide solution are alternately added in portions in such a way that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18.

(Eluant: $H_2O$/tetrahydrofuran: 0–30%).

Yield: 1.34 g (96% of theory) of a reddish-brown powder
Water content: 7.8%
Elementary analysis (relative to anhydrous substance):
Cld: C 41.59 H 4.17 N 10.95 Gd 17.57 Co 3.29 Cl 1.98 Na 2.57
Fnd: C 41.48 H 4.32 N 10.84 Gd 17.43 Co 3.14 Cl 1.81 Na 2.31

EXAMPLE 4 a) [7,12-Diethyl-3,8,13,17-tetramethylporphyrin-2,18-dipropionylhydrazinato(2-)-K N21, K N22, K N23, K N24]-copper 1190 mg (2 mmol) of 3,3'-(7,12-diethyl-3,8,13,17-tetramethylporphyrin-2,18-diyl)-di(propanohydrazide), produced analogously to H. Fischer, E. Haarer and F. Stadler, Z. Physiol. Chem. 241, 209 (1936), and 523.5 mg (2 mmol) of copper(II)-are heated in 150 ml of acetic acid/100 ml of chloroform for 5 hours to 80° C. Then, it is concentrated by evaporation in a vacuum, the residue is suspended in water, filtered off and washed with water. The dried crude product is recrystallized from pyridine/diethyl ether.

Yield: 1.19 g (91% of theory) of a reddish-brown powder

| Elementary analysis: | | | | |
|---|---|---|---|---|
| Cld: | C 62.22 | H 6.14 | N 17.07 | Cu 9.68 |
| Fnd: | C 62.10 | H 6.33 | N 16.92 | Cu 9.51 | b) [7,12-Diethyl-3,8,13,17-tetramethyl-2,18-bis{3,6,18-trioxo -8,11,14-tris(carboxymethyl)-17-oxa-4,5,8,11,14-pentaazanonadec-1-yl}-porphinato(2-)]-copper 806.8 mg (2 mmol) of 3-ethoxy-carbonylmethyl-6-[2—(2,6-dioxomorpholino)ethyl]-3,6-diaza octanedioic acid (DTPA-monoethylester-monoanhydride) is suspended in 250 ml of absolute dimethylformamide. It is covered with a layer of nitrogen, 1.01 g (10 mmol) of triethylamine and 656 mg (1 mmol) of the title compound of Example 4a are added, and the resulting reaction mixture is stirred for 3 days at room temperature. After the reaction is completed, it is filtered, the solvent is drawn off in a vacuum, and the remaining oil is pulverized with 500 ml of diethyl ether. The precipitated solid is filtered off and washed with diethyl ether and n-hexane. For purification, it is chromatographed on silica gel RP-18 (eluant: $H_2O$/tetrahydrofuran: 0–30%).

Yield: 1.27 g (87% of theory) of a reddish-brown powder
Water content: 6.2%

| Elementary analysis (relative to anhydrous substance): | | | | |
|---|---|---|---|---|
| Cld: | C 54.18 | H 6.20 | N 13.40 | Cu 4.34 |
| Fnd: | C 54.02 | H 6.31 | N 13.29 | Cu 4.18 | c) [7,12-Diethyl-3,8,13,17-tetramethyl-2,18-bis{3,6,18-trioxo-8,11,14-tris(carboxymethyl)-4,5,8,11,14-pentaazahexadecanoato}porphinato (2-)]-copper 1.24 g (0.848 mmol) of the ligand that is produced under Example 4b is dissolved in 400 ml of water. By adding 10 mol of aqueous sodium hydroxide solution, the pH is set at 13 and stirred for 5 hours at room temperature. After the ester groups have been completely saponified, a pH of 3 is set with concentrated hydrochloric acid. It is evaporated to the dry state in a vacuum. The residue is chromatographed on silica gel RP 18 (eluant: $H_2O$/tetrahydrofuran/gradient).

Yield: 1.15 g (96% of theory) of a reddish-brown powder
Water content: 4.4%

| Elementary analysis (relative to anhydrous substance): | | | | |
|---|---|---|---|---|
| Cld: | C 52.93 | H 5.87 | N 13.94 | Cu 4.52 |
| Fnd: | C 52.83 | H 6.04 | N 13.85 | Cu 4.38 | d) {Mu-[{16,16'-[copper(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium 1.12 g (0.796 mmol) of the ligand that is produced under Example 4c is dissolved in 400 ml of water, and 420 mg (1.59 mmol) of gadolinium chloride and 2N aqueous sodium hydroxide solution are alternately added in portions in such a way that the pH of the reaction mixture constantly varies between 6.8 and 7.2. If all of the gadolinium chloride is added, stirring is continued overnight at room temperature. For working-up, the solvent is drawn off in a vacuum, and the residue is chromatographed on silica gel RP-18.

(Eluant: $H_2O$/tetrahydrofuran: 0–30%).

Yield: 1.37 g (98% of theory) of a reddish-brown powder
Water content: 7.6%

| Elementary analysis (relative to anhydrous substance): | | | | | |
|---|---|---|---|---|---|
| Cld: | C 42.32 | H 4.24 | N 11.15 | Gd 17.88 | Cu 3.61 | Na 2.61 |
| Fnd: | C 42.18 | H 4.38 | N 11.09 | Gd 17.70 | Cu 3.48 | Na 2.47 |

EXAMPLE 5 a) Acetato {7,12-diethyl-3,8,13,17-tetramethyl-2,18-bis[15,15-dimethyl-3,6,13-trioxo-8-(2-{N,N-bis[(t butoxycarbonyl)methyl]amino}-ethyl)-11-[(t butoxy-carbonyl)-methyl]14-oxa-4,5,8,11-tetraazahexadec-1-yl}-porphyrinato (3-) manganese 8.31 g (13.45 mmol) of 3,9-bis(t butoxycarbonyl)methyl]-6-carboxymethyl-3,6,9-triazaundecanedioic acid-di-t-butylester, and 2.09 g (15 mmol) of 4-nitrophenol are dissolved in 60 ml of dimethylformamide, and 5.16 g (25 mmol) of N,N'-dicyclohexylcarbodiimide is added at 0° C. It is stirred for 3 hours at DOC, then overnight at room temperature. 2.37 g (3.36 mmol) of the title compound of Example 2a (dissolved in 50 ml of pyridine) is added in drops to the active ester solution that is thus produced, and it is stirred overnight. 100 ml of a 50 aqueous ammonium chloride solution is added, evaporated to the dry state in a vacuum, and the residue is chromatographed on silica gel (mobile solvent: dichloromethane/2-propanol =20:1).

Yield: 5.25 g (83% of theory) of a dark brown solid

| Elementary analysis: | | | | | |
|---|---|---|---|---|---|
| Cld: | C 59.97 | H 7.82 | N 10.42 | Mn 2.92 | Cl 1.88 |
| Fnd: | C 59.83 | H 8.03 | N 10.28 | Mn 2.83 | Cl 1.67 | b) {Mu-[acetatomanganese(III)-{13,13'-[7,12-diethyl-3,8,13,17-tetramethyl-porphyrin-2,18-diyl]-bis{3-carboxymethyl-6-(2-{N,N-bis[(carboxy)methyl]amino}ethyl)-8,11-dioxo-3,6,9,10-tetraazatridecanoato]}(8-)]}digadolinato(2-), disodium 5.25 g (2.79 mmol) of the title compound of Example 5a is dissolved in 100 ml of trifluoroacetic acid and stirred for 8 hours at room temperature. It is evaporated to the dry state in a vacuum. The ligand that is thus obtained is dissolved in 100 ml of water, and 1.01 g (2.79 mmol) of gadolinium oxide is added. It is stirred at 60° C. and kept at a pH of 5 by adding 1N aqueous sodium hydroxide solution. The solution is filtered, and the filtrate is set at pH 7.2 with 1N aqueous sodium hydroxide solution. Then, it is chromatographed on RP 18 (mobile solvent: gradient consisting of water/acetonitrile).

Yield: 4.63 g (93% of theory) of a brown, amorphous solid Water content: 9.2%

| Elementary analysis (relative to anhydrous substance): | | | | | | |
|---|---|---|---|---|---|---|
| Cld: | C 41.69 | H 4.18 | N 10.98 | Mn 3.08 | Cl 1.98 | Gd 17.61 | Na 2.57 |
| Fnd: | C 41.54 | H 4.35 | N 10.82 | Mn 2.91 | Cl 1.85 | Gd 17.45 | Na 2.34 |

EXAMPLE 6 a) {10,10'-(My-acetatomanganese(III)-{10,10'-(7,12-diethyl-3,8,13,17-tetramethylporphyrin-2,18-diyl)bis[[(1RS)-1-methyl-2,5,8-trioxo-3,6,7-triaza-dec-1-yl]}) bis [1,4,7,10-tetraazacyclododecane-1,4,7-triacetato(3-)]}digadolinium 8.47 g (13.45 mmol) of the Gd complex of 10-(4-carboxy-2-oxo-3-aza-1-methyl-butyl)-1,4,7,10-tetraazacyclododecane-1,4,7-triacetic acid, 0.64 g of lithium chloride (15 mmol) and 2.09 g (15 mmol) of 4-nitrophenol are dissolved in 100 ml of dimethyl sulfoxide at 50° C. After cooling to room temperature, 5.16 g (25 mmol) of N,N'dicyclohexylcarbodiimide is added and preactivated for 12 hours. 2.37 g (3.36 mmol) of the title compound of Example 2a and 0.71 g (7 mmol) of triethylamine are added to the solution that is thus produced, and it is stirred overnight at room temperature. The suspension that is obtained is then mixed with sufficient acetone until complete precipitation occurs, and the precipitate is suctioned off, dried, taken up in water, insoluble dicyclohexylurea is filtered off, and the filtrate is chromatographed on RP 18 (mobile solvent: gradient consisting of tetrahydrofuran/water).

Yield: 5.06 g (79Cr of theory) of a dark brown, amorphous powder

Water content: 8.3%

Elementary analysis (relative to anhydrous substance):

| Elementary analysis (relative to anhydrous substance): | | | | | |
|---|---|---|---|---|---|
| Cld: | C 45.36 | H 5.08 | N 13.22 | Gd 16.50 | Mn 2.88 | Cl 1.86 |
| Fnd: | C 45.24 | H 5.21 | N 13.13 | Gd 16.38 | Mn 2.71 | Cl 1.72 |

Fnd: C 45.24 H 5.21 N 13.13 Gd 16.38 Mn 2.71 Cl 1.72

EXAMPLE 7 a) Conjugate of acetato [7,12-diethyl-3,8,13,17-tetramethylporphyrin-2,18-dipropionylhydrazinato (2-)-K N21, K N22, K N23, K N24]-iron and 10-[7-(4-isothiocyanatophenyl)-2-hydroxy-5-oxo-7-(carboxymethyl)-4-aza-heptyl)]-1,4,7-tris (carboxylatomethyl)-1,4,7-tris(carboxylatomethyl)-1,4,7,10-tetraazacyclododecane, gadolinium complex, sodium salt {10,10'-{my-chloroiron(III){10,10'-[(7,12-diethyl-3,8,13,17-tetramethylporphyrin-2,18-diyl)bis{(1-oxopropane-3,1-diyl)hydrazino-thiocarbonylamino-4,1-phenylene[(3RS)-3-carboxymethyl-1-oxopropane-3,1-diyl]amino(2-hydroxypropane-3,1-diyl)}]}bis[1,4,7,10-tetraazacyclododecane-1,4,7-triacetato (4-)]) digadolinium, disodium)

1.01 g (10 mmol) of triethylamine is added to 708 mg (1 mmol) of the title compound of Example la and 1806 mg (2.2 mmol) in 50 ml of water, and it is stirred for 12 hours at room temperature. It is evaporated to the dry state in a vacuum and chromatographed on silica gel (mobile solvent: methanol/water/glacial acetic acid=10/5/1). The product-containing fractions are evaporated to the dry state, the residue is dissolved in 100 ml of water and set at pH 7.2 with 2N sodium hydroxide solution.

Then, it is freeze-dried.

Yield: 2.11 g (92% of theory) of a dark brown, amorphous powder

Water content: 8.5%

Elementary analysis (relative to anhydrous substance):

Cld: C 44.95 H 5.09 N 12.19 Cl 1.54 Fe 2.43 S 2.79 Gd 13.69 Na 2.00

Fnd: C 44.83 H 5.19 N 12.03 Cl 1.38 Fe 2.38 S 2.58 Gd 13.48 Na 1.78

EXAMPLE 8

Production of a formulation of {mu-[(16,16'-[chloroiron (III)-7,12-diethyl-3,8,13,17-tetramethylporphyrin-2,18- diyl]-bis[3,6,9-tris(carboxymethyl)-11,14-dioxo-3,6,9,12, 13-pentaazahexadecanoato]}(8-)])-digadolinato(2-), disodium (addition of mannitol)

50 mmol of the title compound of Example 1d, 10 mmol of tris-buffer (tris(hydroxy-methyl)aminomethane hydrochloric acid of pH 7.4) and 120 mmol of mannitol are dissolved in 500 ml of bidistilled water and made up with water to a volume of 1 1 in a measuring flask. The solution that is thus obtained is filtered via a 0.2 μm membrane and decanted in a vial. A solution that is thus produced can be used directly for NMR diagnosis.

EXAMPLE 9

Production of a formulation of {mu-[{16,16'-[chloromanganese(III)-7,12-diethyl-3,8,13,17-tetramethylporphyrin-2,18-diyl]-bis[3,6,9-tris (carboxymethyl)-11,14-dioxo-3,6,9,12,13-pentaazahexadecanoato]}(8-)]}-digadolinato(2-), -disodium (addition of common salt)

10 mmol of the title compound of Example 2d, 10 mmol of tris-buffer (tris(hydroxy-methyl)aminomethane hydrochloric acid of pH 7.4) and 60 mmol of sodium chloride are dissolved in 500 ml of bidistilled water and made up with water to a volume of 1 1 in a measuring flask. The solution that is thus obtained is filtered via a 0.2 μm membrane and decanted in a vial. A solution that is thus produced can be used directly for NMR diagnosis.

EXAMPLE 10

MRI Experiments on Animals with Induced Myocardial Infarction

The necrosis-selective enhancement was studied after one-time intravenous administration of the substance of Example 1d on animals with experimentally produced myocardial infarction in the MRI experiment. The induction of the myocardial infarction was carried out on anesthetized (Domitor$^{(R)}$/Dormicum$^{(R)}$, i.m.) rats (Han Wistar, Schering SPF, about 300 g of body weight) by occlusion of the left coronary artery. The contrast medium administration (dose: 100 μmol of Gd/kg of body weight) was carried out about 24 hours after the induction of infarction. The animals were studied before and up to 24 hours after contrast medium administration by MR tomography (SISCO SIS 85, 2 tesla; SE sequence, EKG-triggered, $T_R$: about 400 ms, $T_E$: 10 ms, nt=4, ni=256, FOV: 7*7 cm, SD≈3 mm, 1 layer each axially). About 24 hours p.i., the animals were sacrificed—in the MRT—by an overdose of narcotics, and an MRI experiment on "freshly sacrificed" animals (→ no artifacts of movement) was additionally performed. To verify the infarction (size and position), the heart was prepared, sliced into disks and then NBT ("vital-") staining was performed. Before contrast medium administration, the infarcted area cannot be distinguished from the "normal" myocardium, since both areas are presented isointensively (see FIG.: 1a). Immediately after the administration of substance, the non-perfused portion of the myocardium presents as a hypointense area (see FIG.: 1b). Starting about 30 minutes p.i., the signal intensity in the non-perfused area increases somewhat, while the size of the delimited a (signal-free) area decreases (→ slow diffusion into the necrosis). In the middle and v.a. late phases (starting 2.5 to about 24 hours p.i.), a considerable enhancement in the necrotic area of the myocardium is noted (see FIG.: 1c, d, e). The delineation of the necrotic area in the MRI experiment correlates very readily with the results of the histological "vital" staining.

EXAMPLE 11

MRI Experiments on Animals with Induced Myocardial Infarction The necroselective enhancement was studied after one-time intravenous administration of the substance of Example 2d on animals with experimentally produced myocardial infarction in the MRI experiment. The induction of the myocardial infarction was carried out on anesthetized (Domitor$^{(R)}$/Dormicum$^{(R)}$, i.m.) rats (Han Wistar, Schering SPF, about 300 g of body weight) by occlusion of the left coronary artery. The contrast medium administration (dose: 100 mol of Gd/kg of body weight) was carried out about 24 hours after the induction of infarction. The animals were studied before and up to 3 hours (continuously) as well as 24 hours after contrast medium administration by MR tomography (SISCO SIS 85, 2 tesla; SE sequence, EKG-triggered, $T_R$: about 400 ms, $T_E$: 10 ms, nt=4, ni=256, FOV: 7*7 cm, SD=3 mm, 1 layer each axially). About 24 hours p.i., the animals were sacrificed—in the MRT—by an overdose of narcotics and an MRI experiment on "freshly sacrificed" animals (→ no artifacts of movement) was performed. To verify the infarction (size and position), the heart was prepared, sliced into disks and then NBT (nitro blue tetrazolium chloride) staining was performed. Before contrast medium administration, the infarcted area cannot be distinguished from the "normal" myocardium, since both areas are presented isointensively (see FIG.: 2a). Immediately after the administration of substance, the non-perfused portion of the myocardium presents as a hypointense area (see FIG.: 2b). Starting about 30 minutes p.i., the signal intensity in the non-perfused area increases somewhat, while the size of the delimited (signal-free) area decreases (→ slow diffusion into the necrosis). In the middle and v.a. late phases (starting 2.5 to about 24 hours p.i.), a considerable enhancement in the necrotic area of the myocardium is noted (see FIG.: 2c, 2d). The delineation of the necrotic area in the MRI experiment correlates very readily with the results of the histological NET ("vital") staining.

EXAMPLE 12

MRI Experiments on Animals with Induced Myocardial Infarction

The necrosis-selective enhancement was studied after one-time intravenous administration of the substance of Example 4d on animals with experimentally produced myocardial infarction in the MRI experiment. The induction of the myocardial infarction was carried out on anesthetized (Domitor$^{(R)}$/Dormicum$^{(R)}$, i.m.) rats (Han Wistar, Schering SPF, about 300 g of body weight) by occlusion of the left coronary artery. The contrast medium administration (dose: 100 μmol of Gd/kg of body weight) was carried out about 24 hours after the induction of infarction. The animals were studied before and up to 3 hours (continuously) as well as 24 hours after contrast medium administration by MR tomography (SISCO SIS 85, 2 tesla; SE sequence, EKG-triggered, $T_R$: about 400 ms, $T_E$: 10 ms, nt=4, ni=256, FOV: 7*7 cm, SD=3 mm, 1 layer each axially). About 24 hours p.i., the animals were sacrificed—in the MRT—by an overdose of narcotics, and an MRI experiment on "freshly sacrificed" animals (→ no artifacts of movement) was performed. To verify the infarction (size and position), the heart was prepared, sliced into disks and then NBT (nitro blue tetrazolium chloride) staining was performed. Before contrast medium administration, the infarcted area cannot be distinguished from the "normal" myocardium, since both areas are presented isointensively (see FIG.: 3a). Immediately after the administration of substance, the non-perfused portion of the myocardium presents as a hypointense area (see FIG.: 3b). Starting about 30 minutes p.i., the signal intensity in the non-perfused area increases somewhat, while the size of the delimited (signal-free) area decreases (→ slow diffusion into the necrosis). In the middle and v.a. late phases (starting 2.5 to about 24 hours p.i.), a considerable enhancement in the necrotic area of the myocardium is noted (see FIG.: 3c, 3d). The delineation of the necrotic area in the MRI experiment correlates very readily with the results of the histological NBT ("vital-") staining.

EXAMPLE 13
Effect of Light ($ED_{50}$) on a Tumor Cell Culture in the Presence of Porphyrins In 25 ml culture flasks, a cell culture of human colon carcinoma (HT-29 P9) is reproduced for 3 days at 37° C. The cultures are divided into two groups and diluted with solutions of the test substances (50 mmol of porphyrin unit (PE)/l, diluted with fetal calf serum) in increasing amounts (0; 1.5; 5; 8.5; 12; 15.5; 19 μmol of PE/l). The samples are irradiated for three days with a xenon lamp (8.5 k Lux, UV filter). The first group contains 2 irradiations of a 30-minute duration each daily at an interval of 4 hours. For the rest of the time, it remains in the dark in an incubator. The second group is not exposed to light and remains for the entire time in the dark in the incubator. On the fourth day, the cell growth is determined by live-dead coloration and counting with the counting chamber.

The table indicates the concentration at which about half of the cells are no longer vital.

| Compound | $ED_{50}$ [mmol of PE/l] |
|---|---|
| I | >1.25 |
| II | >1.25 |
| III | >1.25 |
| IV | $6.4 \cdot 10^{-3}$ |

I Compound of Example 1d
II Compound of Example 2d
III Compound of Example 4d
IV Compound of Example 1c, DE 423 2925

IV: of {mu-[{16,16'-1-(7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), -disodium

EXAMPLE 14
Determination of the Compatibility of the Title Compound of Example 2d The acute compatibility of the title compound of Example 2d is to be studied in mice after one-time intravenous administration.

| Test: | |
|---|---|
| Test method: | Method KM D1, 5th Edition |
| Animal subjects: | SPF mice (NMRI, Schering), 18–22 g, f:m = 50:50 |
| Injection rate: | 2 ml/minute |
| Criterion of action: | exitus letalis |
| Observation period: | 7 days |

EXAMPLE 15
Determination of Relaxivity R1 [L $mmol^{-1}.s^{-1}$]
Device: Minispec PC 20

Measurement at 40° C.; 0.47 tesla
Ti-sequence: 180°-TI-90°, inversion recovery

| Substance | Concentration in the feedstock [mmol/L] | Medium | R1 |
|---|---|---|---|
| 1d | 0.19–0.71 n = 3 | water | 11.9 ± 1.0 |
| 2d | 0.22–0.84 n = 3 | water | 9.3 ± 0.1 |
| 4d | 0.23–0.84 n = 3 | water | 11.0 ± 0.1 |
| 1c, DE 4232925 | 0.05–0.5 n = 3 | water | 9.2 ± 0.1 |

EXAMPLE 16
In Vivo Comparison, Title Compound of

EXAMPLE 1d with Dy-DTPA with Respect to Blood Kinetics

As test animals, three 250 g male (Schering-SPF) rats were used. 0.5 ml of a contrast medium mixture consisting of the compound of Example 1d (45 mmol of Gd/l), referred to below as compound 1, and the dysprosium complex of (Dy-DTPA, 57 mmol of Dy/l), referred to below as compound 2, were intravenously administered to each animal. The dose that was thus administered was 82 μmol of Gd/kg (compound 1) or 103 μmol of Dy/kg (compound 2). Blood samples were removed via a catheter in the common carotid artery at the following times: 1, 3, 5, 10, 15, 20, 30, 45, 60, 90, 120 minutes p.i. In the blood samples that are obtained, in each case the concentrations of gadolinium (Gd) and dysprosium (Dy) were measured in parallel using atomic emission spectrometry (ICP-AES). The proportion of injected contrast medium compound 1 (Gd) and compound 2 (Dy, comparison substance) that remains in the blood space can be compared by the different labeling in the same animal. Using special software (Topfit program), the α-t½ and β-t½ elimination half-lives, the distribution volumes as well as the total clearance for blood and plasma can be calculated from the blood or plasma concentrations. These data thus provide information on the compounds remaining in the intravascular space, the distribution ratios in the organism and the elimination.

Figure 4:
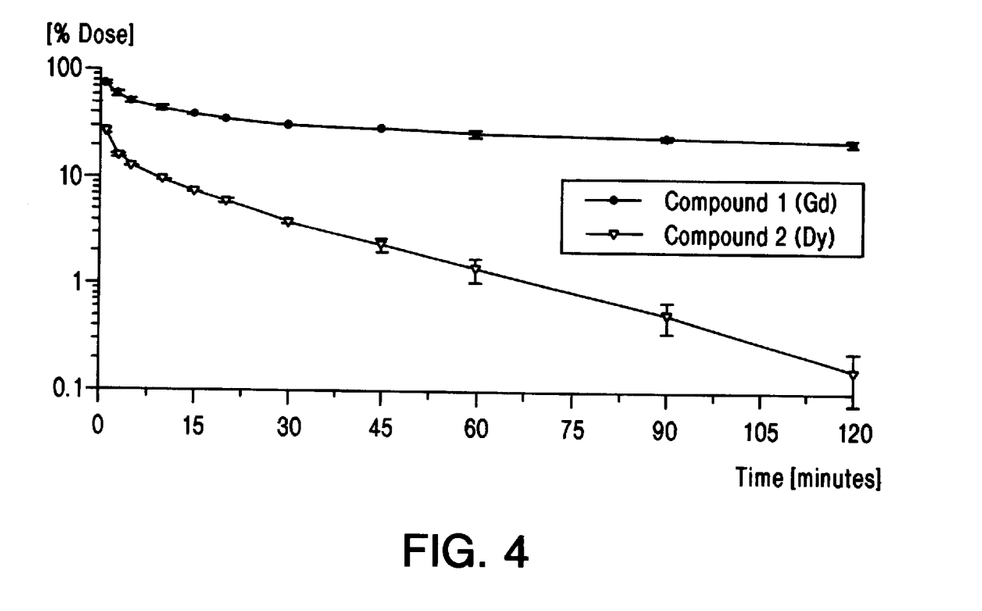

Results: The blood elimination kinetics of compound 1 is clearly distinguished from that of the extracellular contrast medium (compound 2) (see FIG. 4, Table 1). After three minutes, the blood concentrations are still approximately 56–63%. of the dose, and after 120 minutes, approximately 22–25% of the dose. The excretion/diffusion into the tissue is considerably slowed (half-life 173 minutes). The distribution volume and the total clearance are also considerably smaller compared to Dy-DTPA, i.e., compound 1 is not distributed like compound 2 into the intravascular space (vessels) and into the extracellular space, but rather for the most part only into the intravascular space (blood-pool properties of this porphyrin).

The long dwell time of compound 1 in the blood indicates very strong plasma protein bonding. The compound that is described in the example thus meets the requirements of a blood-pool agent.

|  |  | Compound 1 | Compound 2 |
| --- | --- | --- | --- |
| α – t½ | minutes | 3.56 ± 1.01 | 1.19 ± 0.24 |
| β – t½ | minutes | 172.90 ± 38.76 | 18.64 ± 2.47 |
| Vd ss | L/kg | 0.08 ± 0.00 | 0.19 ± 0.01 |
| Total Clearance | ml/min * kg | 0.34 ± 0.07 | 7.74 ± 0.56 |

Table 1: Pharmacokinetic Parameters (Plasma), as well as Elimination Half-lives of Compound 1 in Comparison to Compound 2 in Rats (n=3).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding German application 198 35 082.1 filed Jul. 24, 1998, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A porphyrin-complex of formula I

(I)

wherein atomic numbers 20–32, 37–39, 42–51 or 57–83,
M stands for a paramagnetic ion,
$R^1$ stands for a hydrogen atom, a straight-chain $C_1$–$C_6$ alkyl, a $C_7$–$C_{12}$ aralkyl, or OR',
R' is a hydrogen atom or $C_1$–$C_3$ alkyl,
$R^2$ stands for —(C=Q)(NR$^4$)$_o$—(A)$_q$—(NR$^5$)—K, —CO—Z or —(NH)$_o$—(A)$_q$—NH—D,
Z is —OL,
L is an inorganic cation, an organic cation or a $C_1$–$C_4$ alkyl,
A means a phenylenoxy group, a $C_1$–$C_{12}$ alkylene, a $C_1$–$C_{12}$ alkylene which is interrupted by one or more oxygen atoms, or a $C_7$–$C_{12}$ aralkylene,
o and q, independently of one another, mean numbers 0 or 1,
D means a hydrogen atom or —CO—A—(COOL)$_o$ —(H)$_m$, with m equal to 0 or 1 and the sum of m and o equal to 1,

Q stands for an oxygen atom or for two hydrogen atoms,
$R^3$ stands for —(C=Q)(NR$^4$)$_o$—(A)$_q$—(NR$^5$)—K,
Q stands for an oxygen atom or for two hydrogen atoms,
$R^4$ means a group —(A)$_q$—H,
K means a complexing agent of formula (IIc), (IId), (IIe) or (IIf), whereby $R^5$ has the same meaning as D, provided that a direct oxygen-nitrogen bond is not allowed,

(IIc)

(IId)

(IIe)

(IIf)

in which
$A^1$ means a phenylenoxy group, a $C_1$–$C_{12}$ alkylene, a $C_1$–$C_{12}$ alkylene which is interrupted by one or more oxygen atoms, or a $C_7$–$C_{12}$ aralkylene,
$R^6$ stands for a hydrogen atom, a straight-chain or branched $C_1$–$C_7$ alkyl, a phenyl or benzyl group,
$A^2$ stands for phenylene, —CH$_2$—NHCO—CH$_2$—CH(CH$_2$COOH)—C$_6$H$_4$-β-, —C$_6$H$_4$—O—(CH$_2$)$_{0-5}$-β-, —C$_6$H$_4$—(OCH$_2$CH$_2$)$_{0-1}$—N (CH$_2$COOH)—CH$_2$-β a $C_1$–$C_{12}$ alkylene, or $C_7$–$C_{12}$ alkylene that is optionally interrupted by one or more oxygen atoms, 1 to 3 —NHCO or 1 to 3 —CONH and is optionally substituted by 1 to 3 —(CH$_2$)$_{0-5}$COOH, whereby β stands for the binding site to X, X stands for a —CO— or NHCS group, and $L^1, L^2, L^3$ and $L^4$, independently of one another, stand for a hydrogen atom or a metal ion equivalent of an element of atomic numbers 20–32, 37–39, 42–51 or 57–83, provided that at least two of $L^1, L^2, L^3$ and $L^4$ stand for said metal ion equivalents, and that other anions are present to compensate for optionally present charges in the metalloporphyrin, and free carboxylic acid groups that are not required for complexing are optionally present as salts with physiologically compatible inorganic cations, organic cations, or as esters or amides.

2. A complex according to claim 1, wherein $A^2$ stands for a —CH$_2$——(CH$_2$)$_2$—, —CH$_2$OC$_6$H$_4$-β, —CH$_2$OCH$_2$—, —C$_6$H$_4$—, —C$_6$H$_4$—OCH$_2$-β, —C$_6$H$_4$—OCH$_2$CH$_2$—N(CH$_2$COOH)CH$_2$-β, or —CH$_2$—NHCO—CH$_2$—CH(CH$_2$COOH)—C$_6$H$_4$-β group, whereby β stands for the binding site to X.

3. A complex according to claim 1, wherein X stands for a CO group.

4. A complex according to claim 1, wherein $R^6$ stands for a hydrogen atom or a methyl group.

5. A complex according to claim 1, wherein M stands for an $Fe^{3+}$, $Mn^{3+}$, $Cu^{2+}$, $Co^{3+}$, $VO^{2+}$, $Cr^{3+}$ or $Ni^{2+}$ ion.

6. A complex according to claim 1, wherein $R^2$ and $R^3$ in each case stand for a —CONHNHK, —CONH(CH$_2$)$_2$NHK, —CONH(CH$_2$)$_3$NHK, —CONH(CH$_2$)$_4$NHK or —CONH(CH$_2$)$_2$O(CH$_2$)$_2$NHK group.

7. A complex according to claim 6, wherein $R^2$ and $R^3$ are the same.

8. A complex according to claim 1, wherein q is o.

9. A complex according to claim 11, wherein A is

—CH$_2$—CH$_2$—,
—CH$_2$CH$_2$CH$_2$—,
—CH$_2$CH$_2$CH$_2$CH$_2$—,

—CH$_2$CH$_2$—O—CH$_2$CH$_2$—,
—CH$_2$CH$_2$—O—CH$_2$CH$_2$—O—CH$_2$CH$_2$—,

—(CH$_2$)$_5$—,
—(CH$_2$)$_6$—,
—(CH$_2$)$_{10}$—,
—(CH$_2$CH$_2$—O—)$_2$—CH$_2$CH$_2$—O—CH$_2$CH$_2$—, or
—CH$_2$—O—C$_6$H$_4$—.

10. A porphyrin-complex according to claim 1, wherein said complex is:

{mu-[(16,16'-[chloromanganese(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-),-disodium;

{mu[{16,16'-[chloroiron(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-),-disodium; or

[mu[{16,16'-[copper(II)-7,12-diethyl-3,8,13,17-tetramethylporphyrin-2,18 -diyl]-bis[3,6,9-tris(carboxymethyl)-11,14-dioxo-3,6,9,12,13-pentaazahexadecanoato]}(8-)]}-digadolinato(2-),-disodium.

11. In a method of MR imaging comprising imaging a patient for defection of necrosis, infarction or both, the improvement comprising:

administering to said patient an MRI diagnostic agent which is at least one porphyrin complex of formula I (I)

wherein

M stands for a paramagnetic ion, $R^1$ stands for a hydrogen atom, a straight-chain $C_1$–$C_6$ alkyl, a $C_7$–$C_{12}$ aralkyl, or OR', R' is a hydrogen atom or $C_1$–$C_3$ alkyl, $R^2$ stands for —(C=Q)(NR$^4$)$_o$—(A)$_q$—(NR$^5$)—K, —CO—Z or —(NH)$_o$—(A)$_q$—NH—D, Z is —OL, L is an inorganic cation, an organic cation or a $C_1$–$C_4$ alkyl, A means a phenylenoxy group, a $C_1$–$C_{12}$ alkylene, a $C_1$–$C_{12}$ alkylene which is interrupted by one or more oxygen atoms, or a $C_7$–$C_{12}$ aralkylene, o and q, independently of one another, mean numbers 0 or 1, D means a hydrogen atom or —CO—A—(COOL)$_o$—(H)$_m$, with m equal to 0 or 1 and the sum of m and o is equal to 1,

Q stands for an oxygen atom or for two hydrogen atoms, $R^3$ stands for —(C=Q)(NR$^4$)$_o$—(A)$_q$—(NR$^5$)—K, $R^4$ means a group —(A)$_q$—H, K means a complexing agent of general formula (IIa), (IIb), (IIc), (IId), (IIe) or (IIf), whereby if K is a complexing agent of formula (IIa) then $R^5$ has the same meaning as $R^4$, and if K is a complexing agent of formula (IIb), (IIc), (IId), (IIe) or (IIf), $R^5$ has the same meaning as D, provided that a direct oxygen-nitrogen bond is not allowed, (IIa)

(IIb)

(IIc)

(IId)

(IIe)

(IIf)

$A^1$ means a phenylenoxy group, a $C_1$–$C_{12}$ alkylene, a $C_1$–$C_{12}$ alkylene which is interrupted by one or more oxygen atoms, or a $C_7$–$C_{12}$ aralkylene, $R^6$ stands for a hydrogen atom, a straight-chain or branched $C_1$–$C_7$ alkyl, a phenyl or benzyl group, $A^2$ stands for phenylene, —$CH_2$—NHCO—$CH_2$—CH($CH_2$COOH)—$C_6H_4$-β-, —$C_6H_4$—O—$(CH_2)_{0-5}$-β-, —$C_6H_4$—$(OCH_2CH_2)_{0-1}$—N($CH_2$COOH)—$CH_2$—β a $C_1$–$C_{12}$ alkylene, or $C_7$–$C_{12}$ alkylene that is optionally interrupted by one or more oxygen atoms, 1 to 3 —NHCO or 1 to 3 —CONH and is optionally substituted by 1 to 3 —$(CH_2)_{0-5}$COOH, whereby β stands for the binding site to X, X stands for a —CO— or NHCS group, and $L^1$, $L^2$, $L^3$ and $L^4$, independently of one another, stand for a hydrogen atom or a metal ion equivalent of an element of atomic numbers 20–32, 37–39, 42–51 or 57–83, provided that at least two of $L^1$, $L^2$, $L^3$ and $L^4$ stand for said metal ion equivalents, and that other anions are present to compensate for optionally present charges in the metalloporphyrin, and free carboxylic acid groups that are not required for complexing are optionally present as salts with physiologically compatible inorganic cations, organic cations, or as esters or amides.

12. A method according to claim 11, wherein M stands for an $Fe^{3+}$, $Mn^{3+}$, $Cu^{2+}$, $Co^{3+}$, $VO^{2+}$, $Cr^{3+}$ or $Ni^{2+}$ ion.

13. A method according to claim 11, wherein $R^2$ and $R^3$ in each case stand for a —CONHNHK, —CONH$(CH_2)_2$NHK, —CONH$(CH_2)_3$NHK, —CONH$(CH_2)_4$NHK or —CONH$(CH_2)_2$O$(CH_2)_2$NHK group.

14. A method according to claim 11, wherein q is 0.

15. A method according to claim 11, wherein A is
—$CH_2$—$CH_2$—,
—$CH_2CH_2CH_2$—,
—$CH_2CH_2CH_2CH_2$—,

—$CH_2CH_2$—O—$CH_2CH_2$—,
—$CH_2CH_2$—O—$CH_2CH_2$—O—$CH_2CH_2$—,

—$(CH_2)_5$—,
—$(CH_2)_6$—,
—$(CH_2)_{10}$—,
—$(CH_2CH_2$—O$)_2$—$CH_2CH_2$—O—$CH_2CH_2$—, or
—$CH_2$—O—$C_6H_4$—.

16. A method according to claim 13, wherein $R^2$ and $R^3$ are the same.

17. A method according to claim 11, wherein $A^2$ is a —$CH_2$—, —$(CH_2)_2$—, —$CH_2OC_6H_4$-β, —$CH_2OCH_2$—, —$C_6H_4$—, —$C_6H_4$—$OCH_2$-β, —$C_6H_4$—$OCH_2CH_2$—N($CH_2$COOH)$CH_2$-β, or —$CH_2$—NHCO—$CH_2$—CH($CH_2$COOH))—$C_6H_4$-β group, whereby β stands for the binding site to X.

18. A method according to claim 11, wherein X is CO.

19. A method according to claim 11, wherein $R^6$ is H or methyl.

20. A method according to claim 11, wherein said agent is administered in the amount of 1 μmol to 2 mmol/kg of body weight.

21. A method of MRI diagnostic monitoring of photodynamic therapy comprising administering to a patient a photodynamic agent which is paramagnetic, irradiating said agent, and monitoring the photodynamic therapy induced thereby using magnetic resonance imaging, wherein said agent is a complex according to claim 1.

22. A method according to claim 11, wherein said complex is:

{mu-[(16,16'-[chloromanganese(III)-7,12-diethyl-3,8,13, 17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), -disodium;

{mu[{16,16'-[chloroiron(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), -disodium; or

[mu[{16,16'-[copper(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), -disodium.

\* \* \* \* \*